(12) United States Patent
Meeranpillai

(10) Patent No.: US 11,788,952 B2
(45) Date of Patent: Oct. 17, 2023

(54) DETERMINING CONCENTRATION OF OIL IN WATER BY EXTRACTION

(71) Applicant: Saudi Arabian Oil Company, Dhahran (SA)

(72) Inventor: Nagoorpitchai S. Meeranpillai, Al-Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/681,406

(22) Filed: Feb. 25, 2022

(65) Prior Publication Data
US 2023/0273117 A1    Aug. 31, 2023

(51) Int. Cl.
| | |
|---|---|
| *G01N 21/31* | (2006.01) |
| *G01N 1/34* | (2006.01) |
| *G01N 1/38* | (2006.01) |
| *G01N 1/40* | (2006.01) |
| *G01N 33/18* | (2006.01) |

(52) U.S. Cl.
CPC ............ *G01N 21/31* (2013.01); *G01N 1/34* (2013.01); *G01N 1/38* (2013.01); *G01N 1/4077* (2013.01); *G01N 33/1833* (2013.01); *G01N 2001/4083* (2013.01)

(58) Field of Classification Search
CPC ....... G01N 2001/4083; G01N 33/1833; G01N 1/4077; G01N 1/34; G01N 21/31; B04B 1/00
See application file for complete search history.

(56) References Cited

U.S. PATENT DOCUMENTS

| | | |
|---|---|---|
| 5,381,002 A | 1/1995 | Morrow et al. |
| 6,117,682 A | 9/2000 | Lynn et al. |

OTHER PUBLICATIONS

Cruz, "Derivative UV-Vis Spectroscopy of Crude Oil and Asphaltene Solutions for Composition Determination", Jan. 6, 2021 (Year: 2021).*
ThinkTac, "Separating Funnel Model | ThinkTac | DIY Science" https://www.youtube.com/watch?v=QcOXf4xDgFw, Oct. 1, 2021 (Year: 2021).*
Acques Jestin, "A Small Angle Neutron Scattering Study of the Adsorbed Asphaltene Layer in Water-in-Hydrocarbon Emulsions: Structural Description Related to Stability", Jun. 28, 2007 (Year: 2007).*
Shaoqu Xie, "Generic Biphasic Catalytic Approach for Producing Renewable Diesel from Fatty Acids and Vegetable Oils", 2019 (Year: 2019).*
Banda-Cruz et al., "Crude oil UV spectroscopy and light scattering characterization," Petroleum Science and Technology, Jun. 2016, 34(8):732-738, 8 pages.

(Continued)

*Primary Examiner* — Maurice C Smith
(74) *Attorney, Agent, or Firm* — Fish & Richardson P.C.

(57) ABSTRACT

A method is implemented to determine a concentration of oil in a water sample. A specified amount of cyclohexane is added to the water sample to form a mixture. The mixture is stirred. An oil phase is extracted from the mixture. An absorbance value of the extracted oil phase is measured at a specified wavelength in the visible light spectrum. The specified wavelength is in a range of from 390 nanometers (nm) to 600 nm. The concentration of oil in the water sample is determined based on the measured absorbance value of the extracted oil phase.

13 Claims, 3 Drawing Sheets

(56) References Cited

OTHER PUBLICATIONS

Bastow et al., "Ultraviolet spectroscopy for the analysis of oil-in-water effluent using isopropanol as co-solvent," Applied Spectroscopy, 1997, 51(3):318-322, 5 pages.
Higgins, "Environmentally friendly oil in water analysis by FTIR spectroscopy based on ASTM D7678011," Agilent Technologies, 2012, retrieved from URL <https://www.perlan.com.pl/uploaded/AppBundleEntityProductApplication/fileKey/336/5990-9806enappnote630-4500-5500oilwater.pdf>, 6 pages.
Lawson-Wood et al., "FT-IR qualtification of hydrocarbons in environmental water samples based on ASTM D7678," 2015, retrieved from URL <https://labsense.fi/uploads/7/1/9/5/71957143/ft-ir_quantification_of_hydrocarbons_in_environmental_water_samples_based_on_astm_d7678_012499_01_app.pdf>, 4 pages.
Spectrosci.com [online], "Techniques for measuring oil in water," 2016, retried on Dec. 17, 2021 from URL <https://www.spectrosci.com/knowledge-center/resource-library/oil-in-water-and-soil>, 5 pages.

\* cited by examiner

100

DETERMINING CONCENTRATION OF OIL IN WATER BY EXTRACTION

TECHNICAL FIELD

This disclosure relates to determining the concentration of oil in water.

BACKGROUND

Water occurs naturally in oil and gas wells and reservoirs, for example, from an underlying aquifer or from injector wells, and can mix with and be extracted with the produced hydrocarbons. Co-extraction of water along with mineral hydrocarbons requires expensive separation, treatment, and disposal, which in many cases involves re-injection back into the well. Water cut is the ratio of the quantity of water produced to the total quantity of fluids produced from the production well. As hydrocarbons are depleted from a reservoir, the decrease in reservoir pressure allows for increased water migration into the rock formations, resulting in an increase in water cuts over time. Gas oil separation processes separate produced fluid into gas, oil, and aqueous phases. In some cases, produced water (aqueous phase) is injected back into the subterranean formation, is used in hydraulic fracturing, or is treated and disposed.

SUMMARY

This disclosure describes technologies relating to determining the concentration of oil in water, and in particular, by extracting the oil phase from the water using a solvent. Certain aspects of the subject matter described can be implemented as a method for determining a concentration of oil in a water sample. A specified amount of cyclohexane is added to the water sample to form a mixture. The mixture is stirred. An oil phase is extracted from the mixture. An absorbance value of the extracted oil phase is measured at a specified wavelength in the visible light spectrum. The specified wavelength is in a range of from 390 nanometers (nm) to 600 nm. The concentration of oil in the water sample is determined based on the measured absorbance value of the extracted oil phase.

This, and other aspects, can include one or more of the following features. Extracting the oil phase can include transferring the oil phase to a vial and centrifuging the vial at a specified rotational speed for a specified centrifuging time duration. A top layer of fluid in the vial after centrifuging can be the extracted oil phase. The specified rotational speed can be in range of from about 500 revolutions per minute (rpm) to about 1500 rpm. The specified centrifuging time duration can be in a range of from about 30 seconds to about 60 seconds. Extracting the oil phase can include transferring the oil phase to a funnel and draining at least a portion of the oil phase from a bottom portion of the funnel. A remaining portion of the oil phase in the funnel can be the extracted oil phase. A volumetric ratio of the specified amount of cyclohexane to the water sample can be in a range of from about 1:10 to about 1:1. The specified amount of cyclohexane can be in a range of from about 10 milliliters (mL) to about 25 mL. The extracted oil phase can be diluted prior to measuring the absorbance value of the extracted oil phase. Diluting the extracted oil phase can include adding a second specified amount of cyclohexane to a portion of the extracted oil phase. A volumetric ratio of the second specified amount of cyclohexane to the portion of the extracted oil phase can be in a range of from about 4:1 to about 19:1. Determining the concentration of oil in the water sample based on the measured absorbance value of the extracted oil phase can include comparing the measured absorbance value of the extracted oil phase to a plurality of measured absorbance values of a corresponding plurality of standard fluids. Each of the standard fluids can have a concentration of crude oil in a range of from 1 part per million (ppm) to 1000 ppm. The plurality of measured absorbance values of the corresponding standard fluids can include a first plurality of measured absorbance values of the corresponding plurality of standard fluids at a first wavelength of 400 nm. The plurality of measured absorbance values of the corresponding standard fluids can include a second plurality of measured absorbance values of the corresponding plurality of standard fluids at a second wavelength of 420 nm. The plurality of measured absorbance values of the corresponding standard fluids can include a third plurality of measured absorbance values of the corresponding plurality of standard fluids at a third wavelength of 450 nm. The plurality of measured absorbance values of the corresponding standard fluids can include a fourth plurality of measured absorbance values of the corresponding plurality of standard fluids at a fourth wavelength of 390 nm.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes determining the concentration of oil in water, and in particular, by extracting the oil phase from the water using a solvent. Wet crude is an emulsion of oil (hydrocarbons) and water. Wet crude can be flowed to a gas oil separation unit where phases of the wet crude are separated to produce a dry crude oil product and an aqueous phase. The aqueous phase (produced water) may be injected back into the Earth or treated and disposed.

The subject matter described in this disclosure can be implemented in particular implementations, so as to realize one or more of the following advantages. The methods described herein can be implemented onsite at crude oil operations, for example, at a wellsite or at a gas-oil separation plant. The methods described herein can be robust, reliable, and efficient in measuring a concentration of oil in a water sample, especially for water samples that have an oil content in a range of from about 1.0 milligrams per liter (mg/L) to about 2,000 mg/L. The extractive solvent used in the methods described herein is cyclohexane, which is non-toxic and less volatile in comparison to other extractive solvents used in similar crude oil estimating methods. Thus, the methods described herein can mitigate and/or eliminate certain health and safety risks associated with other conventional methods, for example, that use toxic and/or more volatile extractive solvents. The methods described herein can be more reliable, less costly, and easier to maintain (for example, require less maintenance) in comparison to other conventional methods, for example, that use ultraviolet and/or infrared spectroscopy.

Figure 1A:
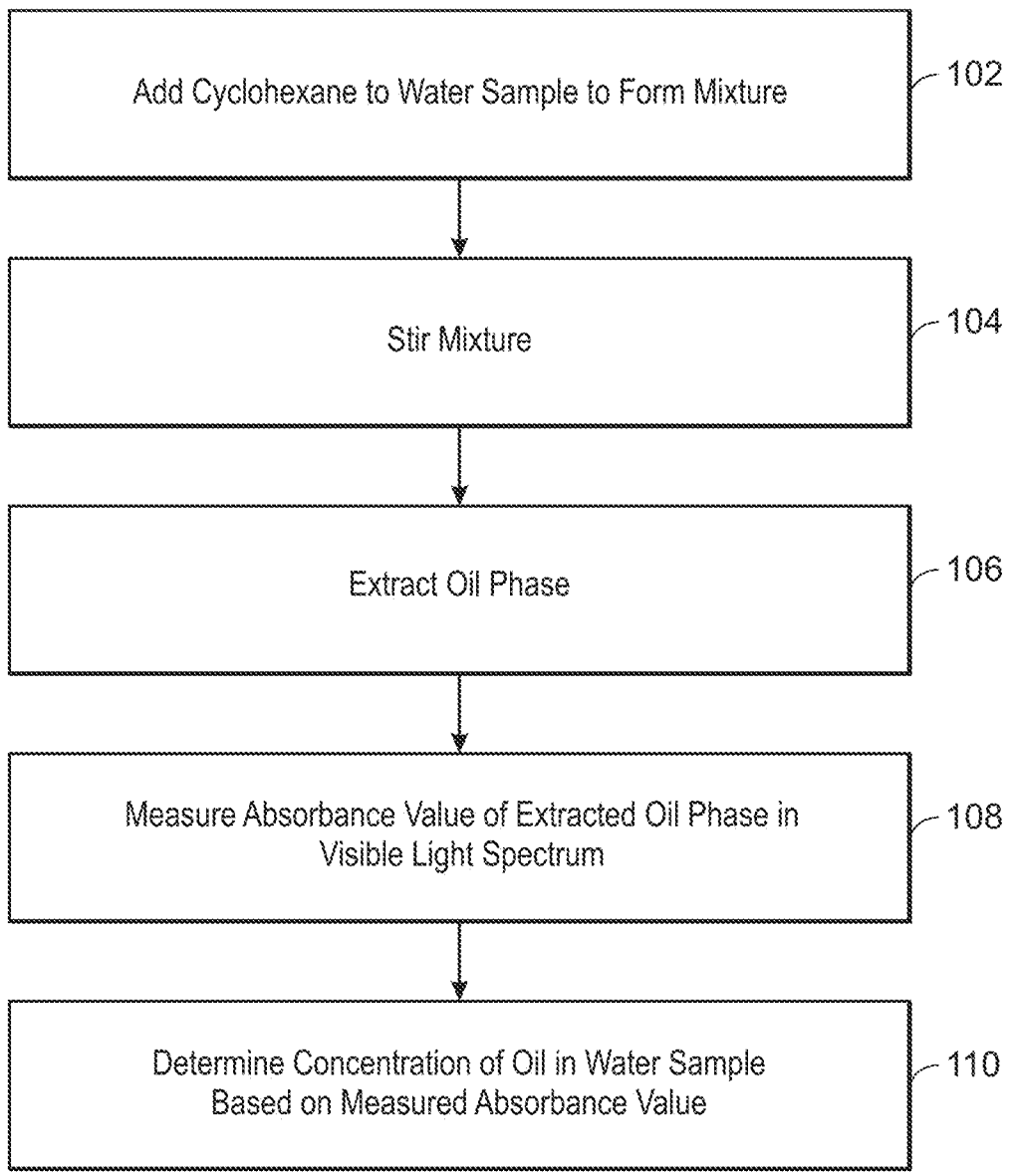
FIG. 1A is a flow chart of an example method for determining a concentration of oil in a water sample.

FIG. 1A is a flow chart of an example method 100 for determining a concentration of oil in a water sample. At block 102, a specified amount of cyclohexane is added to a water sample to form a mixture. In some implementations, a volumetric ratio of the specified amount of cyclohexane to the water sample in the mixture is in a range of from about 1:10 to about 1:1. The specified amount of cyclohexane added to the water sample to form the mixture at block 102 can be, for example, in a range of from about 10 milliliters mL to about 25 mL. At block 104, the mixture is stirred. For example, a magnetic stirrer can be used to stir the mixture at block 104. In some implementations, the mixture is allowed to rest for a specified resting time duration, such that phases of the mixture separate to form an oil phase and a water phase.

At block 106, the oil phase is extracted from the mixture. If, at block 106, the extracted oil phase is too concentrated (for example, has a crude oil concentration of greater than about 1,000 mg/L, greater than about 1,500 mg/L, or greater than about 2,000 mg/L), the extracted oil phase can be diluted ($2^{nd}$ stage dilution) before proceeding to block 108. Diluting the extracted oil phase can include adding a second specified amount of cyclohexane to at least a portion of the extracted oil phase. In some implementations, a volumetric ratio of the second specified amount of cyclohexane to the portion of the extracted oil phase is in a range of from about 4:1 to about 19:1. For example, the volumetric ratio of the second specified amount of cyclohexane to the portion of the extracted oil phase is about 9:1, such that the oil phase extracted at block 106 is diluted by a factor of 10. The $2^{nd}$ stage dilution may be required in cases where instrumentation measurement ranges are narrow (for example, can only measure concentrations up to about 2,000 mg/L). In other cases, the $2^{nd}$ stage dilution may not be required.

At block 108, an absorbance value of the extracted oil phase is measured at a specified wavelength in the visible light spectrum. In some implementations, the specified wavelength at block 108 is in a range of from 390 nanometers (nm) to 600 nm or in a range of from 390 nm to 600 nm. In some implementations, multiple absorbance values of the extracted oil phase are measured at various wavelengths in the visible light spectrum at block 108. Absorbance values of the extracted oil phase can be measured at two wavelengths, three wavelengths, four wavelengths, or more than four wavelengths in the visible light spectrum at block 108. For example, a first absorbance value of the extracted oil phase is measured at a first wavelength of 400 nm. A second absorbance value of the extracted oil phase can be measured at a second wavelength of 420 nm. A third absorbance value of the extracted oil phase can be measured at a third wavelength of 450 nm. In some cases, for example, in cases where the water sample is an effluent originating from an oil refinery, a fourth absorbance value of the extracted oil phase is measured at a fourth wavelength of 390 nm.

At block 110, the concentration of oil in the water sample is determined based on the measured absorbance value(s) of the extracted oil phase (obtained at block 108). In some implementations, determining the concentration of oil in the water sample at block 110 includes comparing the measured absorbance value(s) of the extracted oil phase (obtained at block 108) to measured absorbance value(s) of one or more standard fluids that have been prepared with various known crude oil concentrations. For example, various standard fluids can be prepared with different, specified concentrations of crude oil in a range of from 1 part per million (ppm) to 1,000 ppm. For example, various standard fluids can be prepared with the same concentration of crude oil in a range of from 1 ppm to 1,000 ppm but prepared with different crude oil types (for example, light crude oil, medium crude oil, heavy crude oil, or refinery oil) whose absorbance values are measured at various wavelengths. As one example, a first standard fluid of light crude oil with a concentration of 100 ppm can have an absorbance value of 0.1 at a first wavelength of 400 nm; a second standard fluid of medium crude oil with a concentration of 100 ppm can have an absorbance value of 0.1 at a second wavelength of 420 nm; a third standard fluid of heavy crude oil with a concentration of 100 ppm can have an absorbance value of 0.1 at a third wavelength of 450 nm; and a fourth standard fluid of refinery oil with a concentration of 100 ppm can have an absorbance value of 0.1 at a fourth wavelength of 390 nm. The measured absorbance value(s) of the extracted oil phase (obtained at block 108) can, for example, be compared to the measured absorbance values of the first standard fluid, the second standard fluid, the third standard fluid, the fourth standard fluid, or any combination of these. Determining the concentration of oil in the water sample at block 110 can include comparing the first absorbance value of the extracted oil phase at the first wavelength to the absorbance value(s) of one or more of the standard fluids at the first wavelength. Determining the concentration of oil in the water sample at block 110 can include comparing the second absorbance value of the extracted oil phase at the second wavelength to the absorbance value(s) of one or more of the standard fluids at the second wavelength. Determining the concentration of oil in the water sample at block 110 can include comparing the third absorbance value of the extracted oil phase at the third wavelength to the absorbance value(s) of one or more of the standard fluids at the third wavelength. Determining the concentration of oil in the water sample at block 110 can include comparing the fourth absorbance value of the extracted oil phase at the fourth wavelength to the absorbance value(s) of one or more of the standard fluids at the fourth wavelength.

Extracting the oil phase at block 106 can include transferring the oil phase to a vial and then centrifuging the vial at a specified rotational speed for a specified centrifuging time duration. After centrifugation, the top layer of fluid in the vial is extracted as the extracted oil phase whose absorbance value is measured at block 108. In some implementations, the specified rotational speed is in a range of from about 500 revolutions per minute (rpm) to about 1,500 rpm. For example, the specified rotational speed can be about 1,000 rpm. The specified centrifuging time duration can be in a range of from about 30 seconds to about 60 seconds.

Figure 1B:
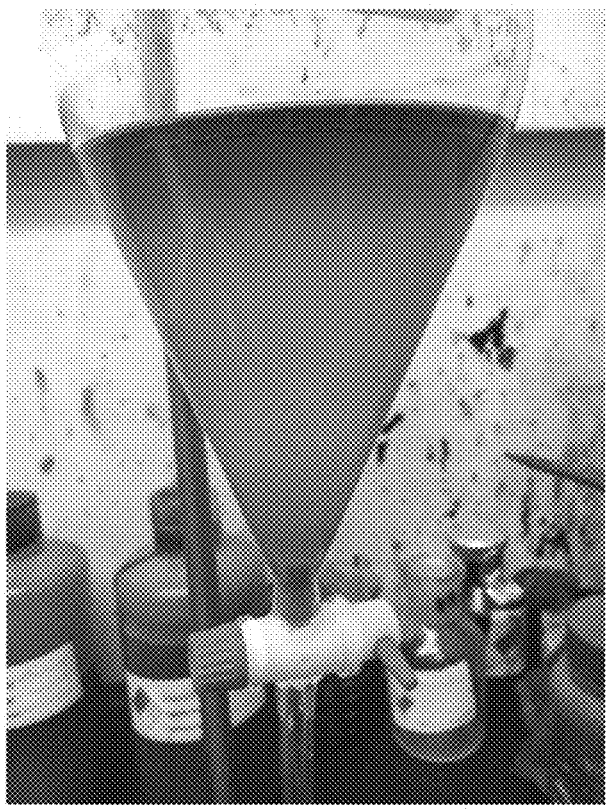
FIG. 1B is a photograph of an oil phase extracted from a water sample and transferred to a funnel.
Figure 1C:
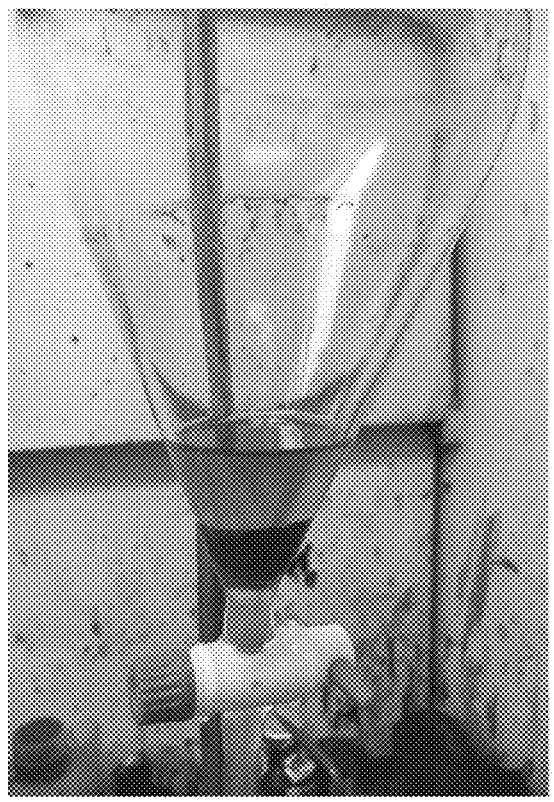
FIG. 1C is a photograph of the oil phase in the funnel after a portion has been drained.

Extracting the oil phase at block 106 can include transferring the oil phase to a funnel and then draining at least a portion of the oil phase from a bottom portion of the funnel. FIG. 1B depicts the oil phase transferred to a funnel. FIG. 1C depicts a remaining portion of the oil phase in the funnel after a portion of the oil phase has been drained from the bottom portion of the funnel. After draining, the top layer of fluid of the remaining portion of the oil phase in the funnel (FIG. 1C) is extracted as the extracted oil phase whose absorbance value is measured at block 108.

Figure 2:
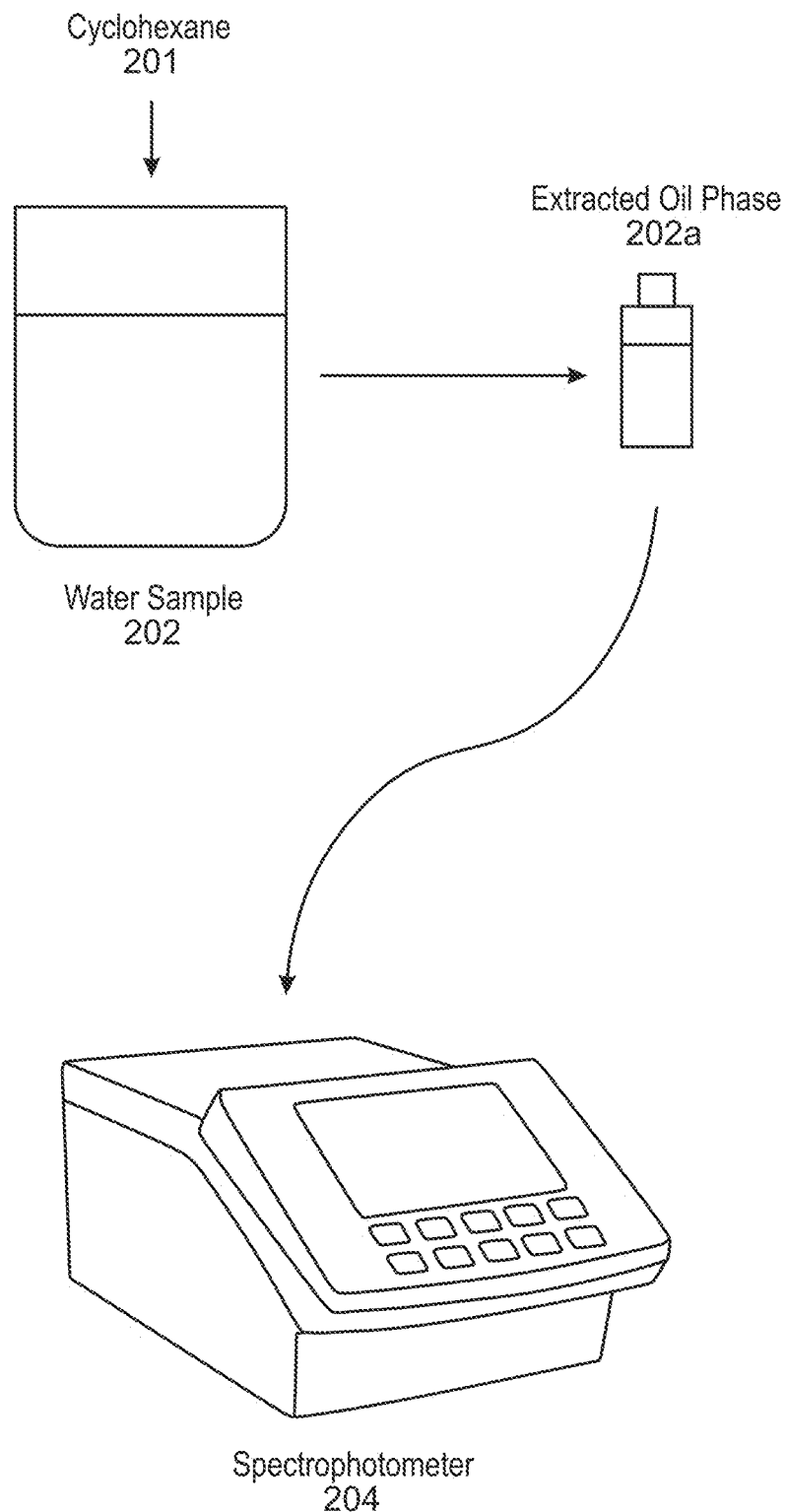
FIG. 2 is a diagram depicting an example progression of the method of FIG. 1A.

FIG. 2 is a diagram 200 depicting a progression of the method 100. Cyclohexane 201 is added to a water sample 202. An oil phase 202a is extracted and input to a spectrophotometer 204. The spectrophotometer 204 measures an absorbance value of the oil phase 202a at a specified wavelength in the visible light spectrum.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any subcombination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A method for determining a concentration of oil in a water sample, the method comprising:
   adding a specified amount of cyclohexane to the water sample to form a mixture, wherein a volumetric ratio of the specified amount of cyclohexane to the water sample is in a range of from about 1:10 to about 1:1;
   stirring the mixture;
   extracting an oil phase from the mixture;
   measuring an absorbance value of the extracted oil phase at a specified wavelength in the visible light spectrum, wherein the specified wavelength is in a range of from 390 nanometers (nm) to 600 nm; and
   determining the concentration of oil in the water sample based on the measured absorbance value of the extracted oil phase.

2. The method of claim 1, wherein extracting the oil phase comprises:
   transferring the oil phase to a vial; and
   centrifuging the vial at a specified rotational speed for a specified centrifuging time duration, wherein a top layer of fluid in the vial after centrifuging is the extracted oil phase.

3. The method of claim 2, wherein the specified rotational speed is in a range of from about 500 revolutions per minute (rpm) to about 1500 rpm, and the specified centrifuging time duration is in a range of from about 30 seconds to about 60 seconds.

4. The method of claim 1, wherein extracting the oil phase comprises:
   transferring the oil phase to a funnel; and
   draining at least a portion of the oil phase from a bottom portion of the funnel, wherein a remaining portion of the oil phase in the funnel is the extracted oil phase.

5. The method of claim 1 wherein the specified amount of cyclohexane is in a range of from about 10 milliliters (mL) to about 25 mL.

6. The method of claim 1 comprising diluting the extracted oil phase prior to measuring the absorbance of the extracted oil phase, wherein diluting the extracted oil phase comprises adding a second specified amount of cyclohexane to a portion of the extracted oil phase.

7. The method of claim 6, wherein a volumetric ratio of the second specified amount of cyclohexane to the portion of the extracted oil phase is in a range of from about 4:1 to about 19:1.

8. The method of claim 1, wherein determining the concentration of oil in the water sample based on the measured absorbance value of the extracted oil phase comprises comparing the measured absorbance value of the extracted oil phase to a plurality of measured absorbance values of a corresponding plurality of standard fluids.

9. The method of claim 8, wherein each of the standard fluids have a concentration of crude oil in a range of from 1 part per million (ppm) to 1000 ppm.

10. The method of claim 9, wherein the plurality of measured absorbance values of the corresponding plurality of standard fluids comprises a first plurality of measured absorbance values of the corresponding plurality of standard fluids at a first wavelength of 400 nm.

11. The method of claim 10, wherein the plurality of measured absorbance values of the corresponding plurality of standard fluids comprises a second plurality of measured absorbance values of the corresponding plurality of standard fluids at a second wavelength of 420 nm.

12. The method claim 11, wherein the plurality of measured absorbance values of the corresponding plurality of standard fluids comprises a third plurality of measured absorbance values of the corresponding plurality of standard fluids at a third wavelength of 450 nm.

13. The method of claim 12, wherein the plurality of measured absorbance values of the corresponding plurality of standard fluids comprises a fourth plurality of measured absorbance values of the corresponding plurality of standard fluids at a fourth wavelength of 390 nm.

\* \* \* \* \*